United States Patent
Tokarski et al.

(10) Patent No.: US 10,661,964 B2
(45) Date of Patent: May 26, 2020

(54) PACKAGES FOR OPHTHALMIC LENSES CONTAINING PHARMACEUTICAL AGENTS

(71) Applicant: Johnson & Johnson Vision Care, Inc., Jacksonville, FL (US)

(72) Inventors: Michael Tokarski, Ponte Vedre, FL (US); Shivkumar Mahadevan, Orange Park, FL (US); Scott Ansell, Jacksonville, FL (US); Vincent Barre, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 701 days.

(21) Appl. No.: 15/468,311

(22) Filed: Mar. 24, 2017

(65) Prior Publication Data
US 2017/0190497 A1    Jul. 6, 2017

Related U.S. Application Data

(63) Continuation of application No. 11/770,778, filed on Jun. 29, 2007, now abandoned.

(60) Provisional application No. 60/819,759, filed on Jul. 10, 2006.

(51) Int. Cl.
| | | |
|---|---|---|
| B65D 81/24 | (2006.01) |
| B65D 81/22 | (2006.01) |
| A45C 11/00 | (2006.01) |
| B65D 75/32 | (2006.01) |
| A61K 31/4535 | (2006.01) |
| B65D 65/40 | (2006.01) |
| B65D 75/36 | (2006.01) |
| B65D 85/00 | (2006.01) |
| B65B 25/00 | (2006.01) |

(52) U.S. Cl.
CPC ............ *B65D 81/22* (2013.01); *A45C 11/005* (2013.01); *A61K 31/4535* (2013.01); *B65D 65/40* (2013.01); *B65D 75/326* (2013.01); *B65D 75/366* (2013.01); *B65D 85/54* (2013.01); *B65B 25/008* (2013.01); *B65D 2585/545* (2013.01)

(58) Field of Classification Search
CPC ... A45C 11/046; A45C 11/005; A45C 11/006; B65D 81/22; B65D 75/326; B65D 75/366; B65D 85/54; B65D 25/008
See application file for complete search history.

(56) References Cited

U.S. PATENT DOCUMENTS

| | | | | |
|---|---|---|---|---|
| 4,691,820 A | * | 9/1987 | Martinez | B65D 75/326 206/205 |
| 6,497,969 B2 | * | 12/2002 | Kim | C08G 73/10 313/502 |
| 6,695,988 B1 | * | 2/2004 | Schlagel | B08B 3/04 264/2.6 |
| 2004/0034042 A1 | * | 2/2004 | Tsuji | A01N 43/90 514/263.31 |
| 2005/0205451 A1 | * | 9/2005 | Brown-Skrobot | A45C 11/005 206/438 |

* cited by examiner

*Primary Examiner* — King M Chu

(57) ABSTRACT

A packaging for an ophthalmic lens containing a pharmaceutical agent.

12 Claims, 10 Drawing Sheets

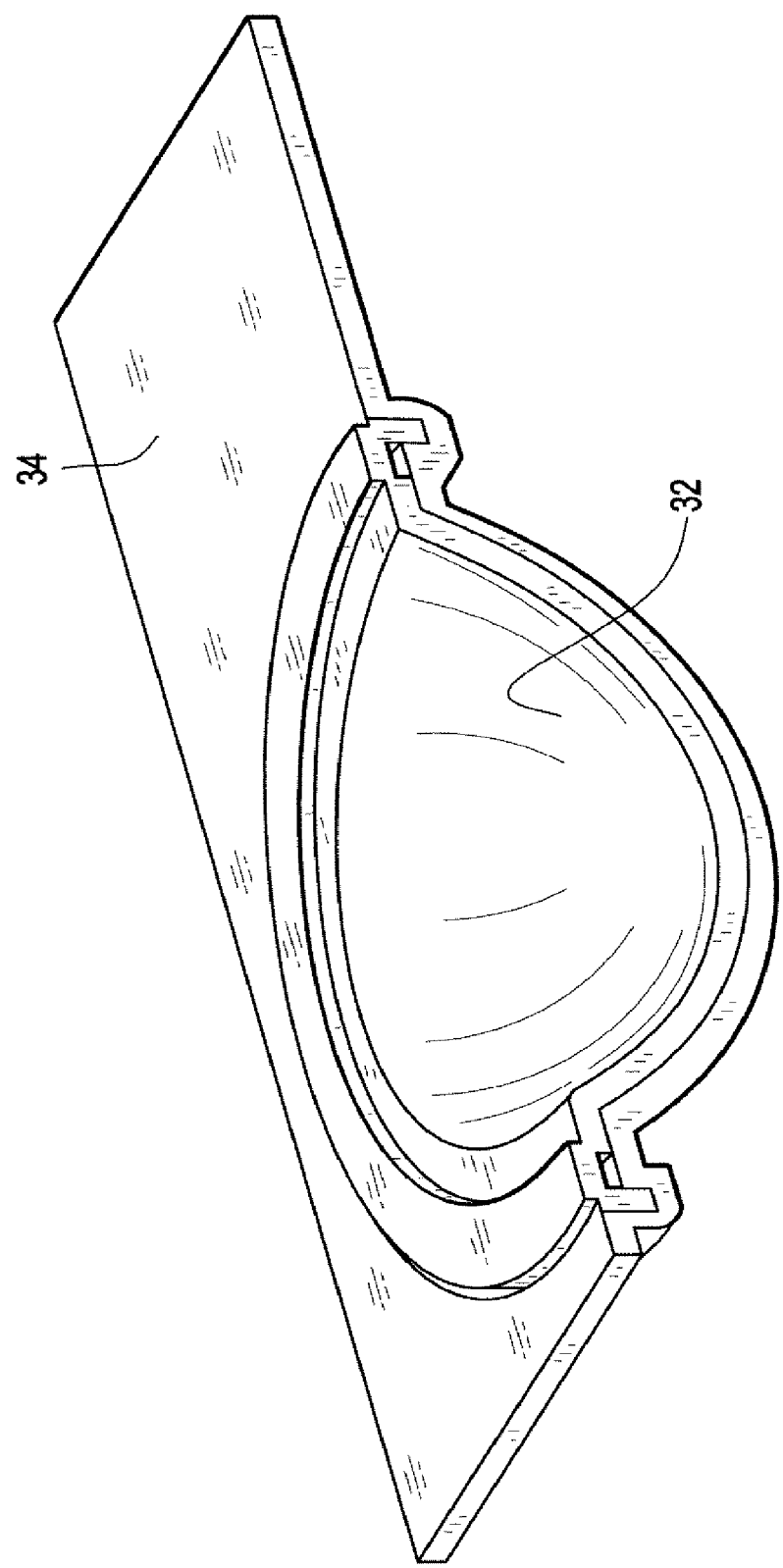

PACKAGES FOR OPHTHALMIC LENSES CONTAINING PHARMACEUTICAL AGENTS

CROSS REFERENCE TO RELATED APPLICATIONS

This application is a continuation of U.S. patent application Ser. No. 11/770,778, filed Jun. 29, 2007 entitled "PACKAGES FOR OPHTHALMIC LENSES CONTAINING PHARMACEUTICAL AGENTS" which is a non-provisional filing claiming priority to expired provisional application, U.S. Ser. No. 60/819,759, filed on Jul. 10, 2006, and entitled "PACKAGES FOR OPHTHALMIC LENSES CONTAINING PHARMACEUTICAL AGENTS," the contents of which are relied upon and incorporated by reference.

FIELD OF THE INVENTION

This invention relates to packages for storing ophthalmic devices that contain pharmaceutical agents, such as ketotifen.

BACKGROUND

Contact lenses have been used commercially to improve vision since the 1950s. At first contact lenses were made of hard materials that were packaged in glass vials, but were uncomfortable for many patients. Later developments, gave rise to softer more comfortable lenses made of hydrophobic hydrogels and generally referred to as soft contact lenses. Due to the ease of producing these lenses, some have suggested that soft contact lenses may be used to deliver pharmaceutical agents to a patient's eyes. Currently soft contact lenses are produced on a large scale and are packaged as individual blister packages having a bowl portion and a foil top. These packages house the soft contact lens and its aqueous packaging solution. The bowl portion is made from a hydrophobic material such as polypropylene. Polypropylene is a commonly used material for contact lens packages. Polypropylene is resilient enough to withstand the sterilization steps of contact lens manufacture, and can be injection molded into a number suitable shapes and sizes. See, U.S. CPat. Nos. 4,691,820; 5,054,610; 5,337,888; 5,375,698; 5,409,104; 5,467,868; 5,515,964; 5,609,246; 5,695,049; 5,697,495; 5,704,468; 5,711,416; 5,722,536; 5,573,108; 5,823,327; 5,704,468; 5,983,608; 6,029,808; 6,044,966; and 6,401,915 for non-limiting examples of such packaging, all of which are hereby incorporated by reference in their entirety. However, the use of polypropylene in the bowl portion of a soft contact lens package can cause problems when the soft contact lens or its packaging solution contain pharmaceutical agents, particularly antihistamines such as ketotifen.

The use of ketotifen as an eye drop to treat the symptoms such as allergic conjunctivitis is known. Applicants have added ketotifen fumarate, a pharmaceutically active salt of ketotifen, to soft contact lenses and packaged those lenses in a polypropylene bowl. However, the packaging of these lenses in a polypropylene bowl causes problems. At the desired drug concentration greater than fifty percent of drug is absorbed by the polypropylene packaging material over time and removed from either or both the soft contact lens and its packaging solution. This is an undesirable condition because if the packaging material absorbs the drug, it will be difficult to determine how much of the drug is available for use by the patient. Therefore it is desirable to find materials suitable for the bowls of blister packages that minimally absorb the drugs contained in either or both the soft contact lens and its packaging solution. This need is met by the following invention.

BRIEF DESCRIPTION OF THE DRAWINGS

FIG. 10 illustrates a perspective view of a portion of a cross section of a blister package

DETAILED DESCRIPTION OF THE INVENTION

Figure 1:
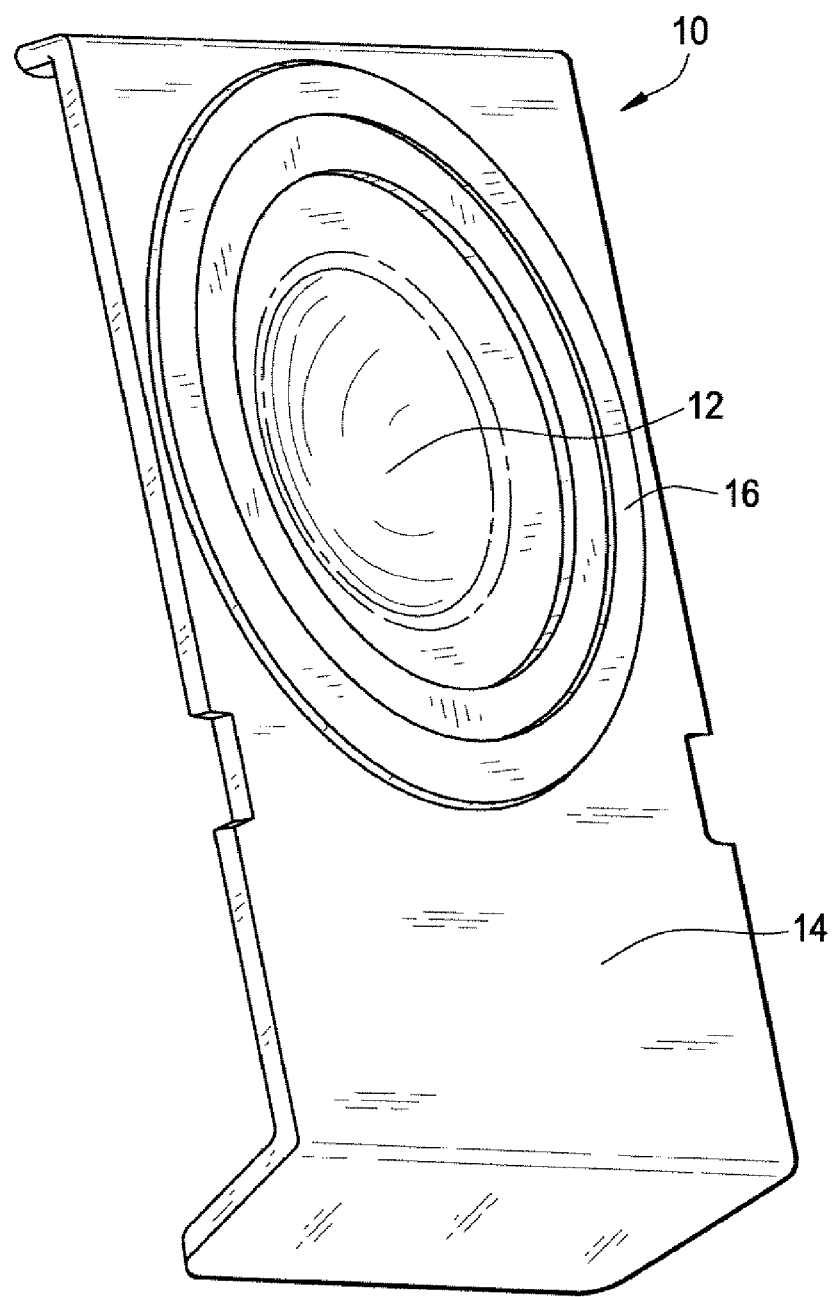
FIG. 1 illustrates the perspective view of a blister package

This invention includes a blister bowl for packaging ophthalmic lens comprising pharmaceutical agents wherein said blister bowl comprises a material that absorbs less than about 16% of said pharmaceutical agents with the proviso that the material is not essentially a perfluoropolymer.

As used herein "ophthalmic lens" refers to a device that resides in or on the eye. These devices can provide optical correction or may be cosmetic. Ophthalmic lenses include but are not limited to soft contact lenses, intraocular lenses, overlay lenses, ocular inserts, and optical inserts. The preferred lenses of the invention are soft contact lenses are made from hydrogels and silicone elastomers, which include but are not limited to silicone hydrogels, and fluorohydrogels. Soft contact lens formulations are disclosed in U.S. Pat. No. 5,710,302, WO 9421698, EP 406161, JP 2000016905, U.S. Pat. Nos. 5,998,498, 6,087,415, 5,760,100, 5,776,999, 5,789,461, 5,849,811, and 5,965,631. The foregoing references are hereby incorporated by reference in their entirety. The particularly preferred ophthalmic lenses of the inventions are know by the United States Approved Names of etafilcon A, genfilcon A, lenefilcon A, lotrafilcon A, lotrafilcon B, balafilcon A, polymacon, bafilcon, acofilcon A acquafilcon A, alofilcon A alphafilcon A, amifilcon A, astifilcon A, atalafilcon A, bisfilcon A bufilcon A, crofilcon A, cyclofilcon A, darfilcon A deltafilcon A, deltafilcon B, dimefilcon A, drooxifilcon A, epsifilcon A, esterifilcon A, focofilcon A, galyfilcon A, govafilcon A, hefilcon A hefilcon B, hefilcon D, hilafilcon A, hilafilcon B, hixoifilcon A, hioxifilcon B, hioxifilcon C, hydrofilcon A, lenefilcon A, licryfilcon A, licryfilcon B, lidofilcon B, lidofilcon A, mafilcon A, mesifilcon A, methafilcon B, mipafilcon A, nelfilcon A, netrafilcon A, ocufilcon A, ocufilcon B, ocufilcon C, ocufilcon D, ocufilcon E, ofilcon A, omafilcon A, oxyfilcon A, pentafilcon A, perfilcon A, pevafilcon A, phemfilcon A, senofilcon A, silafilcon A, siloxyfilcon A, tefilcon A, tetrafilcon A, trifilcon A, vifilcon A, or xylofilcon A. More particularly preferred ophthalmic lenses of the invention are genfilcon A, lenefilcon A, lotrafilcon A, lotrafilcon B, or balafilcon A. The most preferred lenses include but are not limited to galyfilcon, senofilcon, etafilcon A, nelfilcon A, hilafilcon, and polymacon.

Pharmaceutical agents are substances that may be used to treat or to prevent diseases of the eye. Pharmaceutical agents include, but are not limited to antihistamines, antibiotics, antibacterial agents, antiviral agents, antifungal agents, analgesics, anesthetics, antiallergeneic agents, mast cell stabilizers, steroidal and non-steroidal anti-inflammatory agents, angiogenesis inhibitors; antimetabolites, fibrinolytics, neuroprotective drugs, angiostatic steroids, mydriatics, cyclopegic mydriatics; miotics; vasoconstrictors; vasodilators, anticlotting agents; anticancer agents, antisense agents, immunomodulatory agents, carbonic anhydrase inhibitors, integrin antabonistsl; cyclooxygenase inhibitors, VEGF antagonists; immunosuppressant agents, vitamins, supplements and the like. "Antihistamines" are class of pharmaceutical agents that are used to treat allergic conditions. Examples of antihistamines include but are not limited to acrivastine, antazoline, astemizole, azatadine, azelastine, brompheniramine, buclizine, burimamide, carbinoxamine, carebastine, cetirizine, chlorcyclizine, chlorpheniramine, cimetidine, ciproxifam, clemastine, clobenpropit, clozapine, cyclizine, cyproheptadine, desbrompherniramine, desloratadine, dexbrompheniramine, dexchlorpherniramine, diphenhydramine, doxylamine, dimenhydrinate, dimethindene, diphenhydramine, diphenylpyraline, doxylamine, ebastine, efletirizine, emedastine, epinastine, famotidine, fexofenadine, hydroxyzine, impentamine, iodoaminopotentidine, iodophenpropit, ketotifen, levocabastine, levoceterizine, loratadine, meclizine, mepyramine, mequitazine, methdilazine, methapyrilene, mianserin, mifetidine, mizolastine, norastemizole, norebastine, olopatadine, pheniramine, phenyltoxamine, picumast, promethazine, pyrilamine, pyrrobutamin, rantidine, R-sopromidine, S-sopromidine, tecastemizole, temelastine, terfenadine, thiethylperazine, tiotidine, trimeprazine, tripelennamine, thioperamide, triprolidine and pharmaceutically acceptable salts thereof. The preferred antihistamines are ketotifen and pheniramine. The most particularly preferred antihistamines are ketotifen and pharmaceutically acceptable salts thereof. The pharmaceutical agent can be added to the ophthalmic lens by a number of methods. One method to soak a hydrated hydrogel ophthalmic lens in a solution that contains the pharmaceutical agent. Another method is to sterilize a hydrated hydrogel ophthalmic lens in a solution containing the antihistamine. Yet another method is to incorporate the pharmaceutical agents into the ophthalmic lens formulation prior to curing the lens.

The term "blister bowl" refers to the receptacle portion of an ophthalmic lens package. Examples of suitably shaped blister bowls are disclosed in the following documents which are hereby incorporated by reference in their entirety, U.S. Pat. Nos. D 458,023; 4,691,820; 5,054,610; 5,337,888; 5,375,698; 5,409,104; 5,467,868; 5,515,964; 5,609,246; 5,695,049; 5,697,495; 5,704,468; 5,711,416; 5,722,536; 5,573,108; 5,823,327; 5,704,468; 5,983,608; 6,029,808; 6,044,966; and 6,401,915. The receptacle portion of some ophthalmic lens packages is not bowl shaped. For purposes of this invention, the receptacles of those packages are included in the term blister bowl. Examples of such packages include but are not limited to ophthalmic lens packages disclosed in WO 2005/082721, U.S. Pat. No. 7,086,526, WO 03/016175, and US 2004/0238380, which are hereby incorporated by reference in their entirety. As used herein the "material, that absorbs less than about 16% said pharmaceutical agent" is a polymer. These materials can be formed in the appropriate shapes by injection molding, thermoforming, transfer molding, skin packaging, blow molding, coinjection molding, film extrusion, or film coextrusion and the like. It is preferred that the blister bowl is transparent to the degree necessary to permit visual inspection, treatment with steam, UV sterilization and the like.

The amount of the pharmaceutical agent absorbed by any blister bowl is measured by treating the blister bowl (or a known amount of the material that may be formed in a blister bowl) with a solution containing a known amount of a pharmaceutical agent or its pharmaceutically acceptable salt. The treatment of the blister bowl (or the unformed material) can be allowing a solution of the pharmaceutical agent to contact the blister bowl for a period of time at either room temperature or elevated temperatures. The amount of the pharmaceutical agent absorbed into the blister bowl (or unformed material) is measured by HPLC analysis of the solution for its content of pharmaceutical agent, before the treatment and after such treatment. The preferred materials absorb pharmaceutical agents between about 16% and about 0%, more preferably, between about 8% and about 3%, most preferably between about 5% and 1%.

The blister bowl may be formed from materials that can be shaped to accommodate a lens or a lens and its packaging solution, provided such materials meet the absorption criteria above. The preferred materials that form the blister bowl are polysulfone, polyetherimide, or polycarbonate co-polymers. Polysulfone polymer sold by Solvay Advanced Polymers under the tradename UDEL® 1700 (CAS Number 25135-51-7) and RADEL® R-5000 (CAS Number 25839-81-0) are preferred. UDEL is a brand of polysulfone polymers having a glass transition temperature of about 190° C. RADEL R-5000 is a brand of polysulfone sold by Solvay that has a glass transition temperature of about 220° C. Another polysulfone, Ultrason, sold by BASF is also useful in this invention. Ultrason has a glass transition temperature of about 188° C. as determined by differential scanning calorimetry (DCS) at 20° C. per minute. Other brands of polysulfone polymers having a glass transition temperature of about 180° C. to about 230° C. are suitable for use in the invention. Other preferred materials include but are not limited to polyetherimides, sold by General Electric under the tradename Ultem (CAS Number 61128-24-3). Ultem has a glass transition temperature of about 229° C. (as calculated from a VICAT temperature of 219° C. obtained by ASTM 1525) Polycarbonate co-polymers having a glass transition temperature of about 147° C. sold by General Electric under the tradename LEXAN HPB3144 are particularly preferred. For purposes of this invention, if the glass transition temperature of a particular polymer is not known, but the VICAT data is available, the glass transition temperature may be calculated by adding about ten degrees to the VICAT temperature (ASTM D1525, ISO 306, A2LA Accredited).

Such blisters can be made by introducing polymer pellets into an injection molding machine. A reciprocating screw inputs heat and shear in the pellets and melts them. The melt is then injected in a mold using either cold or hot runners (in an alternative method a piston is used, and in yet another method a partially opened mold may be filled and coined into its final shape by closing the mold). The plastic will fill a cavity of design and shape suitable to obtaining the parts disclosed in this invention. The polymer then solidifies under pressure to compensate for part of the shrinkage. After the part is solidified it is further cooled until it reaches a temperature at which it can be handled. The part is then removed from the mold via a mechanical or a pneumatic device and transferred to the machine downsream.

Examples of injection molders that may be used include, but are not limited to, Arburg, Battenfeld, Engel, Husky, Netstal, Sumitomo.

The term "solution" refers to any liquid medium in which a medical device is stored. The preferred solutions include without limitation, saline solutions, other buffered solutions, and deionized water. The preferred aqueous solution is saline solution containing salts including, without limitation, sodium chloride, sodium borate, sodium phosphate, sodium hydrogenphosphate, sodium dihydrogenphosphate, or the corresponding potassium salts of the same. These ingredients are generally combined to form buffered solutions that include an acid and its conjugate base, so that addition of acids and bases cause only a relatively small change in pH. The buffered solutions may additionally include 2-(N-morpholino)ethanesulfonic acid (MES), sodium hydroxide, 2,2-bis(hydroxymethyl)-2,2',2"-nitrilotriethanol, n-tris(hydroxymethyl)methyl-2-aminoethanesulfonic acid, citric acid, sodium citrate, sodium carbonate, sodium bicarbonate, acetic acid, sodium acetate, ethylenediamine tetraacetic acid and the like and combinations thereof. Preferably, the solution is a borate buffered or phosphate buffered saline solution.

Further the invention includes a method of storing an ophthalmic lens comprising a pharmaceutical agent, wherein the method comprises placing said ophthalmic lens in a blister bowl and covering said blister bowl with a cover, wherein said blister bowl comprises a material that absorbs less than about 16% of said pharmaceutical agents, with the proviso that the material of the blister bowl is not essentially a perfluoropolymer. As used herein the terms pharmaceutical agents, ophthalmic lens and blister bowl all have their aforementioned meanings and preferred ranges. The term "cover" means any means of enclosing the ophthalmic lens in the blister bowl. Preferably, the cover is a flexible sheets made from adhesive laminates of an aluminum foil and extruded or co-extruded polymer film that can be sealed to the top surface of the blister bowl in order to form a hermetic seal for the ophthalmic lens. Examples of such materials are disclosed in the following publications, U.S. Pat. Pub. No. 2002/0197478; U.S. Pat. Nos. 6,090,471; 5,908,527; 5,656,362; 5,653,844; and 5,620,087, which are hereby incorporated by reference in their entirety. As used herein, the inner layer of such laminates refers to the layer that is adhered to the bowl by heat sealing or other means. If the blister bowl is made from a polysulfone material, the bowl may be covered with a laminate of several layers having an inner layer of polysulfone which is heat sealed to the bowl. An example of one such layered laminate cover contains the following materials listed in order from the material that is sealed to the bowl to the outermost layer: polysulfone (i.e. UDEL, RADEL) adhesive (i.e. Liofol brand sold by Henkel) aluminum foil adhesive, and polyethylene naptholate or polyphenylsulfone. Another example of a layered laminate contains the following materials listed in order from the material that is sealed to the bowl to the outermost layer polycarbonate co-polymer (i.e. LEXAN) adhesive (i.e. Liofol brand sold by Henkel) aluminum foil adhesive, and polyethylene naptholate or polyphenylsulfone.

Often the ophthalmic lenses comprising pharmaceutical agents are packaged in aqueous solutions such as saline or other buffered solutions. These solutions are generically known as packaging solutions. Some materials that absorb less than about 16% of pharmaceutical agents and are useful to form the blister bowls of the invention are materials that allow water vapor to diffuse out of the blister bowls and covers over time. This loss of water vapor is known to reduce the shelf life of such ophthalmic lenses. In order to improve the shelf life of such agents it would be useful if a portion of the surface of the blister bowls was surrounded by a material that inhibited the diffusion of water vapor. This need is met by the following invention.

The invention includes a blister bowl for packaging ophthalmic lens comprising pharmaceutical agents wherein said blister bowl comprises a lens contacting surface and an outer surface wherein said lens contacting surface comprises a material that absorbs less than about 16% of said pharmaceutical agents and outer surface comprises a vapor barrier material, with the proviso that the material of the lens contacting surface is not essentially a perfluoropolymer. As used herein, ophthalmic lens, pharmaceutical agents, blister bowl, and material that absorbs less than about 16% of said pharmaceutical agents all have their aforementioned meanings and preferred ranges.

Figure 2:
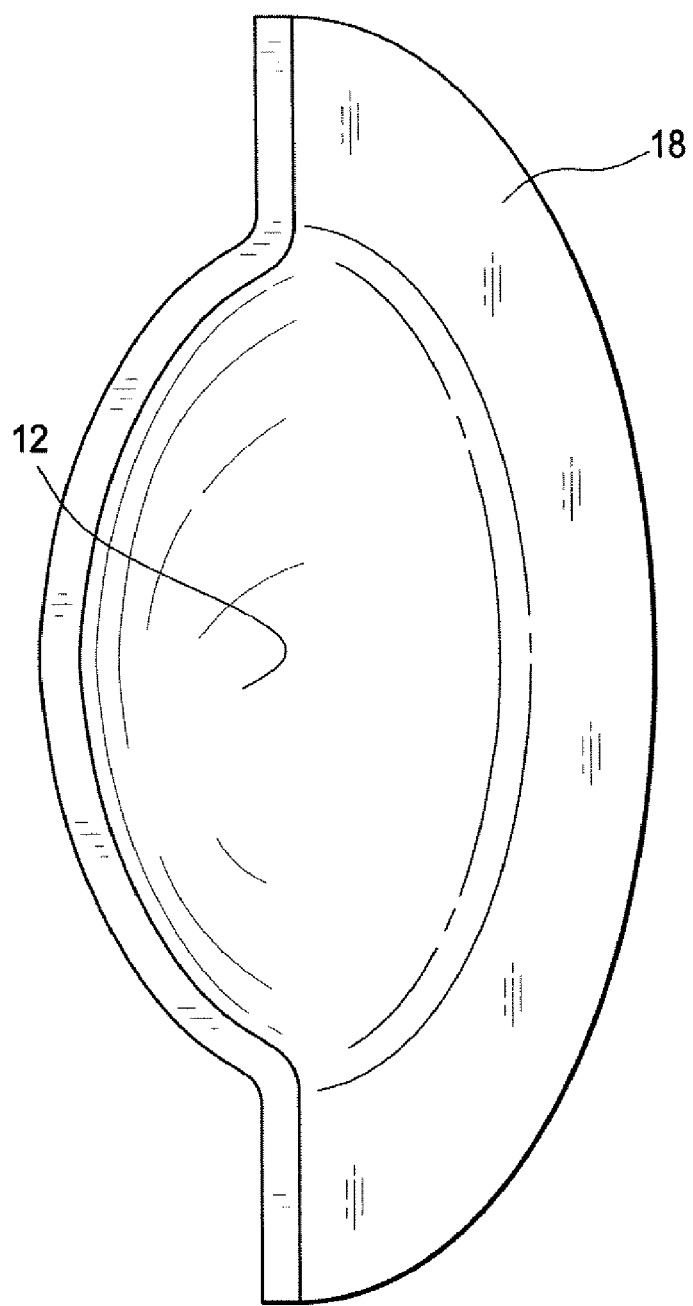
FIG. 2 illustrates a cross sectional view of a portion of a blister package
Figure 3:
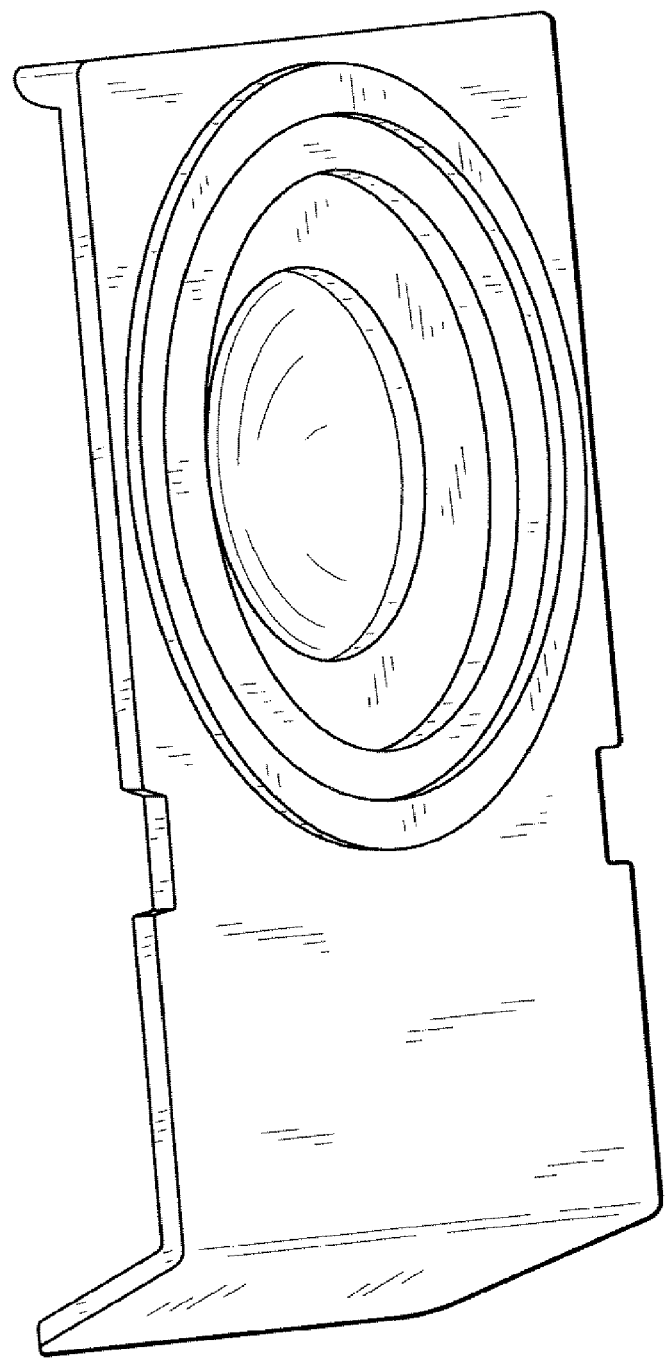
FIG. 3 illustrates the perspective view of a portion of a blister package
Figure 4:
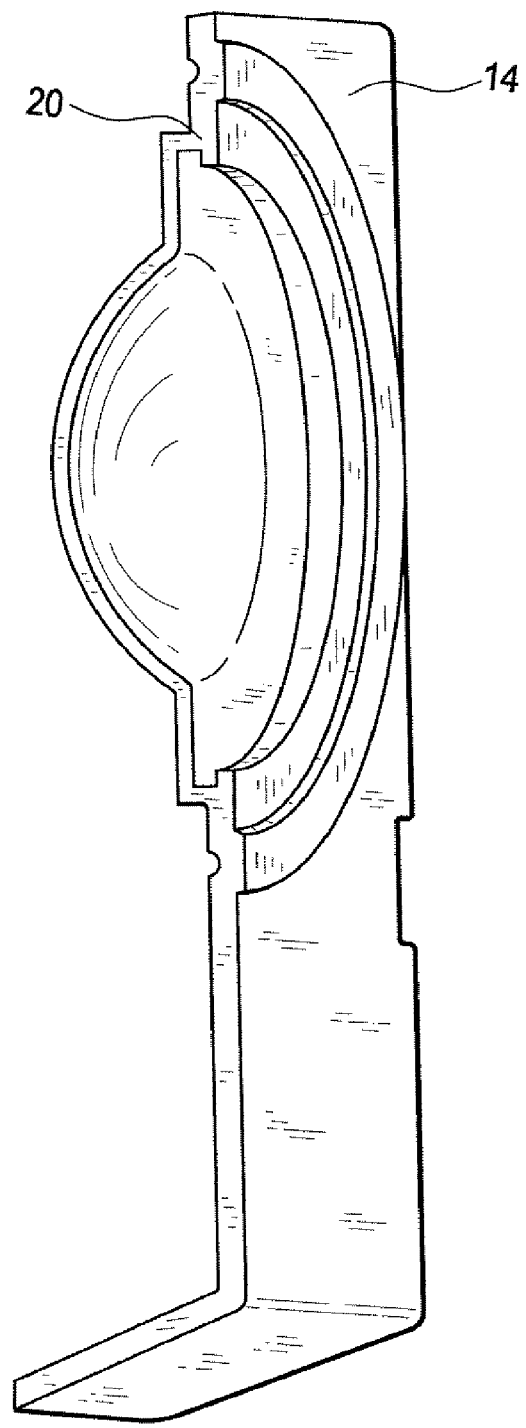
FIG. 4 illustrates the perspective view of a portion of a cross section of a blister package
Figure 5:
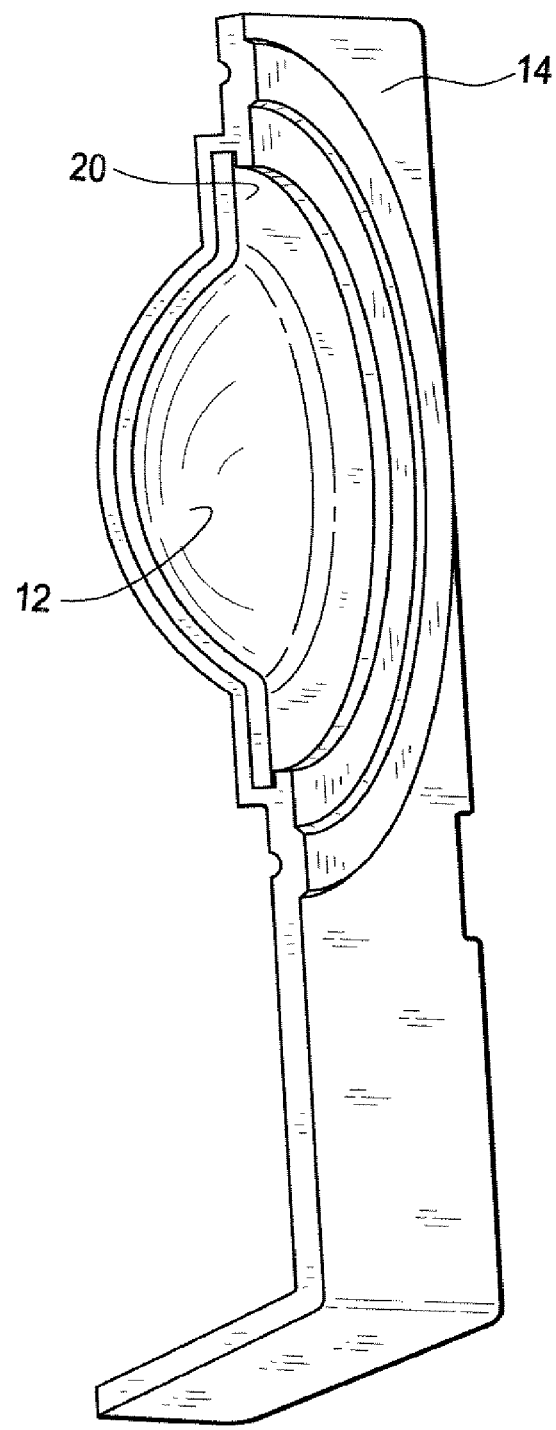
FIG. 5 illustrates a perspective cross sectional view of a portion of a blister package
Figure 6:
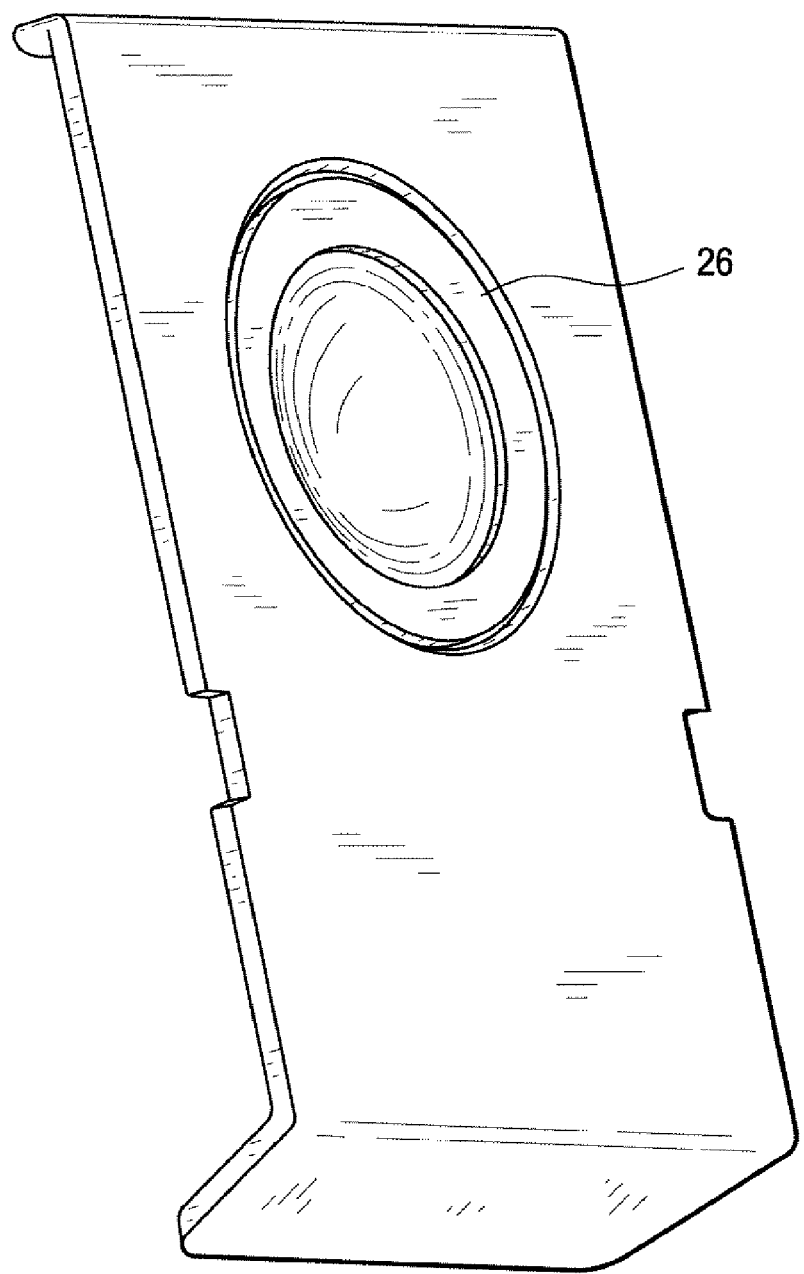
FIG. 6 illustrates the perspective view of a blister package
Figure 7:
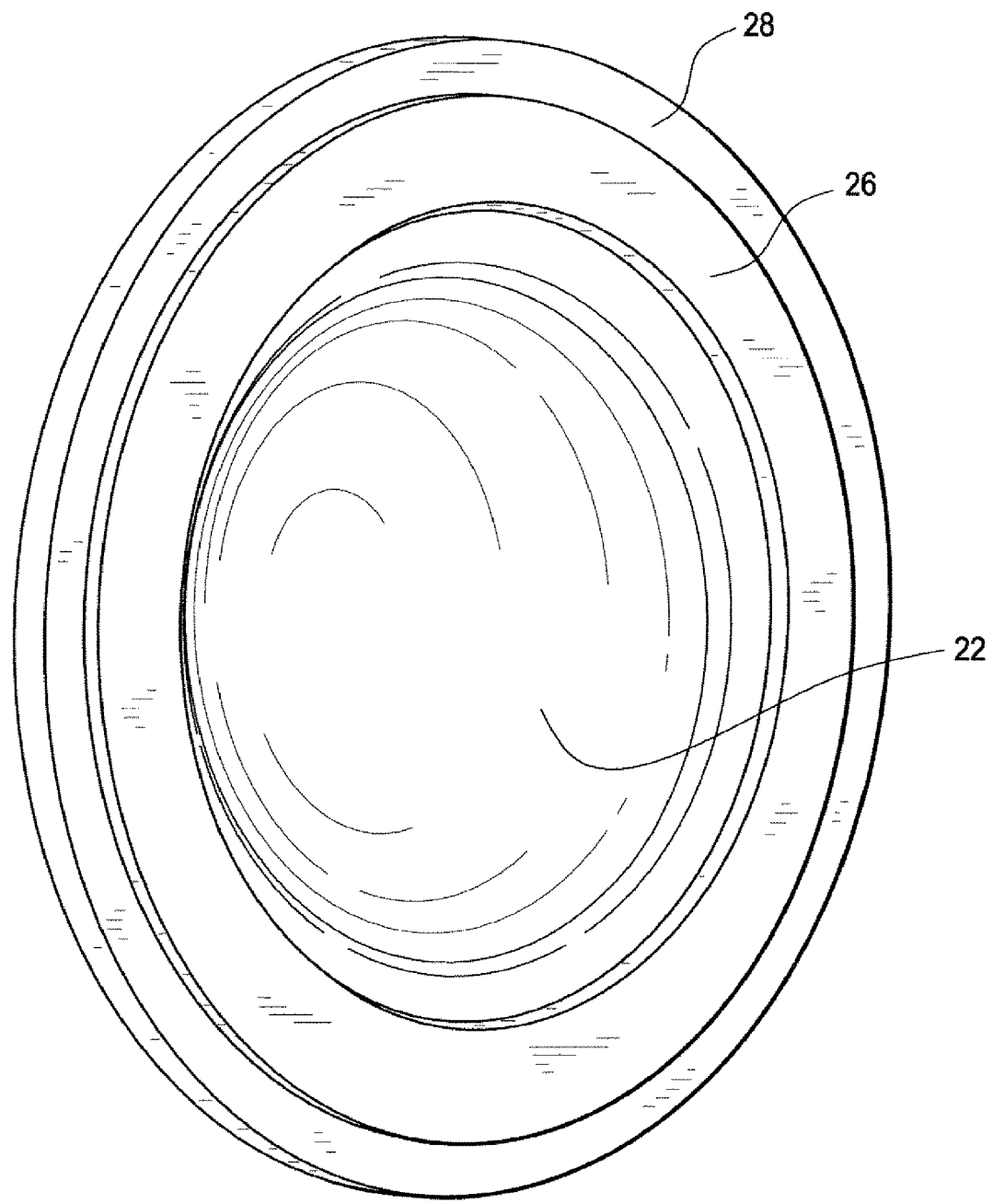
FIG. 7 illustrates a perspective view of a portion of a blister package
Figure 8:
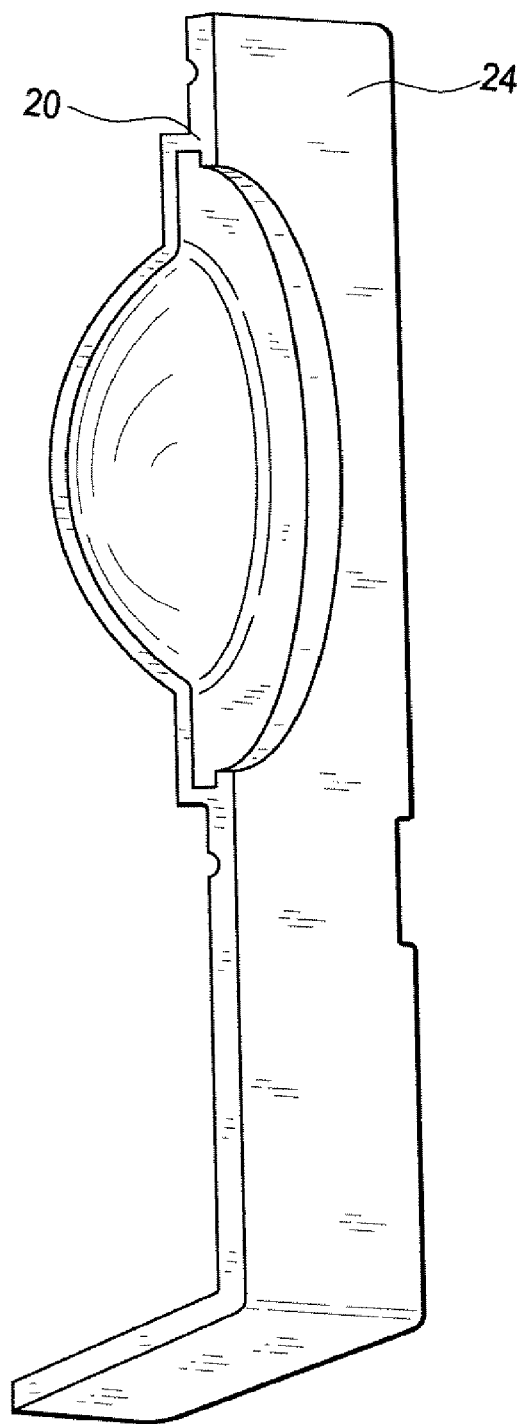
FIG. 8 illustrates a perspective view of a portion of a cross section of a blister package
Figure 9:
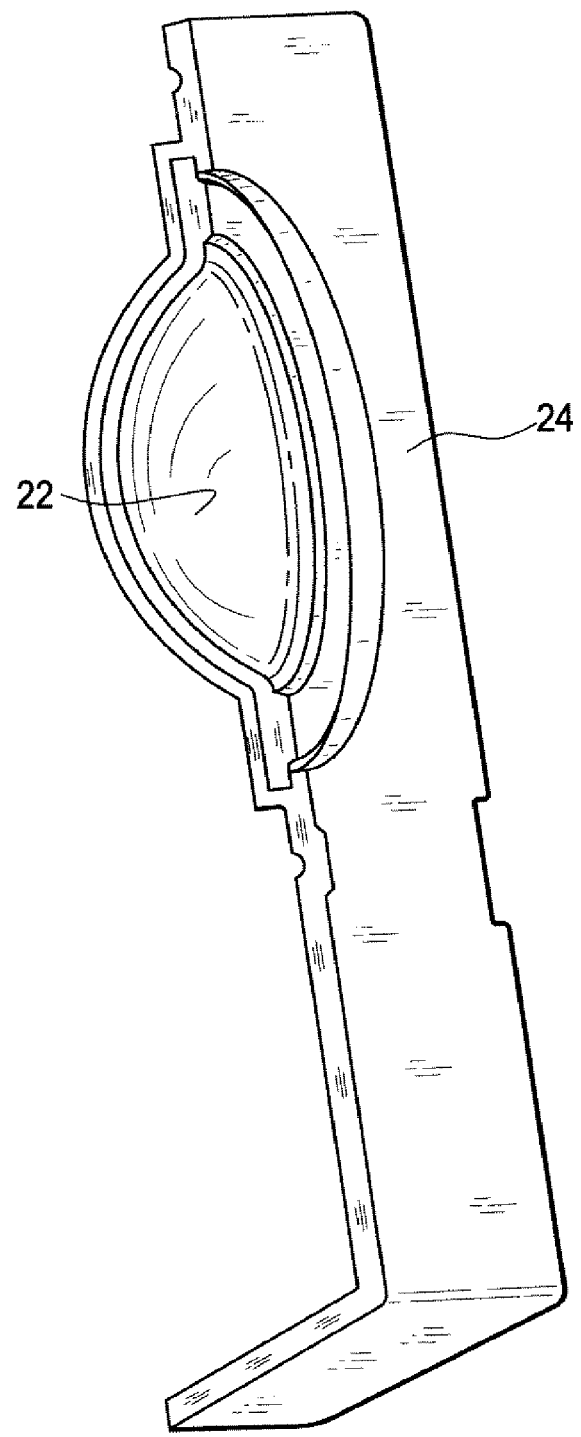
FIG. 9 illustrates a perspective view of a cross section of a blister package

The term "lens contacting surface" refers to the portion of the blister bowl that is in contact with the ophthalmic lens, or with the ophthalmic lens and its packaging solution. The term "outer surface" refers to portions of the bowl other than the lens contacting surface. The term "vapor barrier material" refers to materials that inhibit the diffusion of packaging solutions through the blister bowl. Preferred vapor barrier materials include but are not limited to polypropylene and alicyclic co-polymer contains two different alicyclic monomers sold by Zeon Chemicals L.P. under the tradename ZEONOR. There are several different grades of ZEONOR, having of glass transition temperatures from 70 to 163° C. The particularly preferred ZEONOR, is ZEONOR 1600 or 1420R, which according the to the manufacturer, ZEON Chemicals L.P. has an melt flow rate ("MFR") range of 20 g/10 min for 1420R and 7 g/10 min for 1600 (as tested by JISK 6719 at 280° C.)), a specific gravity ($H_2O=1$) of 1.01 for both as measured by ASTMD792 and a glass transition temperature of 136° C. for 1420R and 163° C. for 1600. The invention is illustrated in further detail by the following figures FIG. 1 illustrates a perspective view of blister bowl 10 of the invention. The lens contacting surface 12 is shaped to house an ophthalmic lens with or without packaging solution. Lens contacting surface 12 is made of materials that absorb less than about 16% of said pharmaceutical agents. Annular sealing ring 16 is raised surface that is sealed with a laminate foil to enclose a lens when blister bowl 10 is closed The preferred lens contacting surface materials are the aforementioned polysulfone and polycarbonate co-polymers described above. The outer surface 14 is a vapor barrier material. The preferred vapor barrier materials are thermoplastics that may be heat sealed and have a vapor barrier sufficient to increase shelf life. The particular preferred vapor barriers are polypropylene and alicyclic co-polymers contains two different alicyclic monomers. FIG. 2 illustrates a cross sectional view of the lens contacting surface 12 and it surrounding flange 18. FIG. 3 illustrates a perspective view of the outer surface 14. FIG. 4 illustrates a perspective cross sectional view of outer surface 14 with internal channel 20. FIG. 5 illustrates outer surface 14 with lens contacting surface 12 inserted into internal channel 20. In the embodiment illustrated by the figures, the surrounding flange 18 is made of the same material as lens contacting surface 12 and surrounding flange 18 is covered and interlocked with the internal channel 20. Another embodiment of the invention is illustrated by FIG. 6. In this embodiment the annular ring, 26 which is used to seal the lens within the blister bowl is located on the surrounding flange 28. FIG. 7 illustrates lens contacting surface 22, its surrounding flange 28 and annular ring 26. FIG. 8 illustrates a perspective cross sectional view of outer surface 24 with internal channel 30. The surrounding flange 28 of lens contacting surface 22 is inserted into the outer surface 24 as illustrated by FIG. 9. FIG. 10, illustrates another embodiment. Len contacting surface 32 is snapped onto a substantially planar flange, 34 that covers the opposite surface of lens contacting surface 32 (not shown). In this embodiment surrounding. In this embodiment it is preferred that lens contacting surface 32 is made from a different material from planar flange 34.

The foregoing blister packs may be made by a variety of 2 plastics processing injection molding machines (overmolding, sandwich molding or insert molding) including but not limited to those manufactured by Arburg Gmbh, Ferromatik, Elektra, Engel, and others. In addition several component injection molding machines may be used to produce multiple layers of vapor barrier materials.

In order to illustrate the invention the following example is included. This example does not limit the invention. They are meant only to suggest a method of practicing the invention. Those knowledgeable in contact lenses as well as other specialties may find other methods of practicing the invention. However, those methods are deemed to be within the scope of this invention.

EXAMPLES

The following abbreviations are used below
Packaging Solution A Deionized water containing the following ingredients by weight: NaCl (0.83%), Boric Acid (0.91%), Sodium tetraborate decahydrate (0.1%), and 0.2% polyacrylic acid sodium salt Example 1

Preparation of Packages with Different Materials

Different solutions of ketotifen fumarate in packing solution A were tested over several experiments to generate the data in Table I (blister materials and amounts of ketotifen are shown in are listed in Table 1. note the fumarate salt of ketotifen was used in solution preparations, but the data reports the amount of ketotifen present in solution). The blister bowl materials (grams listed in Table 1) were cut into small pieces and placed in glass vials with 2.85 mL of ketotifen fumarate solution. The vials were closed with Teflon coated butyl stoppers and heated at 124° C. for 18 minutes. The solutions were extracted and tested by HPLC to determine the concentration of ketotifen (% as compared to control vials without added blister material that were sterilized with the test samples).

TABLE 1

| Material Tradename | Chemical Class | grams material | control conc ketotifen (ug/ml) | percent ketotifen absorbed after treatment |
|---|---|---|---|---|
| UDEL ® 1700 | Polysulfone | 0.505 | 49.31 | 3.4% |
| RADEL ® R-5000 | Polyethersulfone | 0.499 | 49.31 | 4.4% |
| UDEL ® 1700 | Polysulfone | 0.363 | 49.42 | 3.6% |
| RADEL ® R-5000 | Polyethersulfone | 0.363 | 49.42 | 2.4% |
| LEXAN HPB3144 | Polycarbonate copolymer | 0.397 | 48.85 | 10.3% |
| LEXAN HPB3144 | Polycarbonate copolymer | 0.400 | 47.60 | 0.9% |
| Achieve Exxon 1605 | Polypropylene | 0.400 | 49.62 | 30% |
| Ultem | Polyetherimide | 0.400 | 46.60 | 4.6% |
| GE Ultem | Polyetherimide | 0.3634 | 49.42 | 2.1% |
| GE Ultem 1000 | Polyetherimide | 0.3634 | 48.82 | 5.3% |
| GE Ultem 1285 | Polyetherimide | 0.3634 | 48.82 | 4.5% |
| GE Ultem CR55001 | Polyetherimide | 0.3634 | 48.82 | 3.9% |
| GE HPX8R | Polycarbonate copolymer | 0.3634 | 49.25 | 25.6% |
| GE Ultem 1000B | Polyetherimide | 0.3634 | 49.25 | 1.8% |
| GE Valox 315 | polybutylene terephthalate | 0.3634 | 49.25 | 31.5% |
| GE Valox 195 | polybutylene terephthalate | 0.3634 | 49.25 | 29.4% |
| GE EX180 | Polycarbonate Copolymer | 0.4000 | 48.85 | 10.3% |
| GE EX198 | Polycarbonate Copolymer | 0.4000 | 48.85 | 8.5% |
| GE Valox | polybutylene terephthalate | 0.4000 | 48.85 | 94.2% |
| BASF PSF Ultrason | Polysulfone | 0.3634 | 48.82 | 1.5% |
| PET - Mylar (oriented) | polyethylene terephthalate | 0.4000 | 47.60 | 0.2% |
| PFA | perfluoroalkoxy copolymer | 0.4000 | 47.60 | 0.0% |
| FEP | fluorinated ethylene propylene | 0.4000 | 47.60 | 0.0% |
| POM (Delrin) | polyoxymethylene | 0.4000 | 47.60 | 26.8% |
| PVDF (Kynar) | polyvinylidene fluoride | 0.4000 | 47.60 | 8.9% |
| PMMA | PMMA | 0.4000 | 47.60 | 2.6% |
| PEEK | polyetheretherketone | 0.4000 | 47.60 | 0.0% |

TABLE 1-continued

| Material Tradename | Chemical Class | grams material | control conc ketotifen (ug/ml) | percent ketotifen absorbed after treatment |
|---|---|---|---|---|
| Noryl | Modified Polyphenylene Oxide | 0.4000 | 47.60 | 6.8% |
| Halar | Ethylene Chlorotrifluoroethylene | 0.4000 | 47.60 | 14.4% |
| Nylon-6 | Oriented polyamide | 0.4000 | 47.60 | 31.9% |
| POM (Celcon) | polyoxymethylene | 0.4000 | 47.60 | 35.4% |
| PVC (HTP800) | polyvinylchloride | 0.4000 | 47.60 | 17.2% |
| PMP (TPX) | Polymethylpentene | 0.4000 | 47.60 | 9.6% |
| PBT (Hydex) | PolyButylene Teraphalate Polyester | 0.4000 | 47.60 | 27.1% |
| PPS (Techtron) | PolyPhenylene Sulfide | 0.4000 | 47.60 | 3.8% |
| PET (Ertalyte) | Polyethylene terephthalate | 0.4000 | 47.60 | 18.3% |
| PBT (Valox 195) | polybutylene terephthalate | 0.4000 | 47.60 | 15.9% |
| UHMWPE | Ultra high moleculas weight polyethylene | 0.4000 | 47.60 | 32.2% |
| GE FRI 1001 | polybutylene terephthalate | 0.4000 | 47.60 | 9.5% |
| PEI (Ultem) | polyetherimide | 0.4000 | 47.60 | 0.0% |
| PSF (Ultrason) | Polysulfone | 0.4000 | 47.60 | 0.0% |
| GE V2205 | polybutylene terephthalate | 0.4000 | 47.60 | 89.6% |
| PSF (Udel) | polysulfone | 0.4000 | 47.60 | 2.3% |
| GE Xylex | Polycarbonate + Polyester | 0.4000 | 47.60 | 7.1% |
| GE EXRL 0180 | Polycarbonate copolymer | 0.4000 | 47.60 | 0.9% |
| PPS (Techtron) | PolyPhenylene Sulfide | 0.4000 | 47.60 | 16.6% |

What is claimed is:

1. A package containing an ophthalmic lens in solution comprising:
a blister bowl, an ophthalmic lens and a pharmaceutical agent;
said blister bowl with said pharmaceutical agent heated to an elevated temperature above room temperature;
a cover covering said blister bowl;
wherein said blister bowl comprises a material that absorbs less than about 16% of said pharmaceutical agent; and
wherein the material of the blister bowl is polyetherimide.

2. The package of claim 1 wherein the cover comprises an adhesive laminate, comprising an inner layer.

3. The package of claim 1 wherein said blister bowl comprises a material that absorbs less than about 10% of said pharmaceutical agent.

4. The package of claim 1 wherein said polyetherimide has a glass transition temperature of greater than about 220° C.

5. The package of claim 1 wherein said blister bowl comprises a material that absorbs between less than about 8% and about 3% of said pharmaceutical agents.

6. The package of claim 1 further comprising that the pharmaceutical agent is ketotifen fumarate or one of its salts.

7. A package containing an ophthalmic lens in solution comprising:
a blister bowl, an ophthalmic lens and a pharmaceutical agent;
said blister bowl with said pharmaceutical agent heated to an elevated temperature at or above 124 C;
a cover covering said blister bowl;
wherein said blister bowl comprises a material that absorbs less than about 16% of said pharmaceutical agent; and
wherein the material of the blister bowl is polyetherimide.

8. The package of claim 7 wherein the cover comprises an adhesive laminate, comprising an inner layer.

9. The package of claim 7 wherein said blister bowl comprises a material that absorbs less than about 10% of said pharmaceutical agent.

10. The package of claim 7 wherein said polyetherimide has a glass transition temperature of greater than about 220° C.

11. The package of claim 7 wherein said blister bowl comprises a material that absorbs between less than about 8% and about 3% of said pharmaceutical agents.

12. The package of claim 7 further comprising that the pharmaceutical agent is ketotifen fumarate or one of its salts.

* * * * *